(12) United States Patent
Schmitt et al.

(10) Patent No.: US 7,765,092 B2
(45) Date of Patent: Jul. 27, 2010

(54) COMPUTER SYSTEM AND METHOD FOR CALCULATING ADME PROPERTIES

(75) Inventors: Walter Schmitt, Neuss (DE); Jörg Keldenich, Wuppertal (DE); Jannis Batoulis, Leverkusen (DE); Michael Beck, Monheim (DE); Roger-Michael Brunne, Wuppertal (DE); Thorsten Bürger, Köln (DE); Thorsten Pötter, Dormagen (DE); Felix Reichel, Bergisch Gladbach (DE); Stefan Willmann, Düsseldorf (DE)

(73) Assignee: Bayer Technology Services GmbH, Leverkusen (DE)

( * ) Notice: Subject to any disclaimer, the term of this patent is extended or adjusted under 35 U.S.C. 154(b) by 1396 days.

(21) Appl. No.: 10/497,759

(22) PCT Filed: Nov. 25, 2002

(86) PCT No.: PCT/EP02/14150

§ 371 (c)(1),
(2), (4) Date: Jan. 4, 2005

(87) PCT Pub. No.: WO03/048720

PCT Pub. Date: Jun. 12, 2003

(65) Prior Publication Data

US 2005/0119832 A1    Jun. 2, 2005

(30) Foreign Application Priority Data

Dec. 7, 2001   (DE) ............................... 101 60 270

(51) Int. Cl.
*G06G 7/58*     (2006.01)
*G01N 33/48*    (2006.01)

(52) U.S. Cl. .............................. 703/11; 702/19; 702/20; 703/12

(58) Field of Classification Search ....................... None
See application file for complete search history.

(56) References Cited

U.S. PATENT DOCUMENTS 5,751,605 A        5/1998  Heritage et al.
2002/0169561 A1*  11/2002  Benight et al. ................ 702/19

FOREIGN PATENT DOCUMENTS

| EP | 1 167 969 A2 | 1/2002 |
| WO | WO 00 15178 A | 3/2000 |
| WO | WO 00 79268 A | 12/2000 |
| WO | WO 02 10742 A | 2/2002 |

OTHER PUBLICATIONS

Definition for the word "system," from The American Heritage® Dictionary of the English Language, Fourth Edition. Copyright © 2000 by Houghton Mifflin Company. Published by the Houghton Mifflin Company, printed from <http://www.bartleby.com/61/46/S0974600.html> on Mar. 2, 2008.*

Norris D. A. et al. "Development of predictive pharmacokinetic simulation models for drug discovery" Journal of Controlled Release, Elsevier Science Publishers B.V., Amsterdam, NL, Bd. 65, Nr. 1-2, Mar. 2000.

* cited by examiner

*Primary Examiner*—Shubo (Joe) Zhou
(74) *Attorney, Agent, or Firm*—Norris McLaughlin & Marcus, PA; Christa Hildebrand, Esq.

(57) ABSTRACT

A computer system and a method for calculating an ADME properties of a substance on the basis of molecular properties of the substance by using a biophysical model, into which the molecular properties are entered as input quantities. The biophysical model establishes a relationship between the molecular properties and the ADME properties.

8 Claims, 3 Drawing Sheets

|  | Total mass (g) | Water | Fat | Protein |
|---|---|---|---|---|
| Body total | 70000 | 42000 | 13300 | 10600 |
| Subcutaneous cell tissue | 15000 | 2300 | 12000 | 750 |
| Blood | 5500 | 4400 | 36 | 990 |
| Plasma | 3100 | 2900 | 23 | 210 |
| Erythrocytes | 2400 | 1500 | 13 | 780 |
| Brain | 1400 | 1100 | 150 | 110 |
| Gall bladder | 10 | 7.3 | 0 | 0 |
| Digestive tract | 1200 | 950 | 74 | 160 |
| Heart | 330 | 240 | 33 | 55 |
| Kidneys | 310 | 240 | 16 | 53 |
| Liver | 1800 | 1300 | 120 | 320 |
| Lungs | 1000 | 780 | 9.9 | 177 |
| Muscles | 28000 | 22000 | 340 | 4800 |
| Skeleton | 10000 | 3300 | 1900 | 1900 |
| Skin | 2600 | 1600 | 260 | 750 |
| Spleen | 180 | 140 | 2.9 | 35 |
| Testicles | 35 | 28 | 1.1 | 4.2 |

COMPUTER SYSTEM AND METHOD FOR CALCULATING ADME PROPERTIES

CROSS-REFERENCE TO RELATED APPLICATIONS

This application is a 371 of PCT/EP02/14150, filed on Nov. 25, 2002, and claims priority under 35 USC §119 on the basis of German Application No. 101 60 270.7, filed Dec. 7, 2001.

BACKGROUND OF THE INVENTION (1) Field of the Inventions

The invention relates to a computer system and a method for calculating ADME properties of a substance, in particular for a substance with a pharmacological effect or a substance for crop protection uses.

(2) Description of Related Art

The efficacy of active agents is determined by their interaction with the molecular biological target, as well as by the concentration at the target site. The two quantities are generally determined by different molecular parameters, and can therefore be optimized independently of one another within certain limits. While the intrinsic biochemical effect can be determined by in-vitro tests at a very early research stage for large numbers of substances, the concentration at the active site can only be studied through experiments on the whole organism (animal, plant or fungus). This means that the information can only be carried out at late research stages owing to the elaborate nature of the experiments, and is therefore unavailable for the initial optimization cycles.

In recent years, attempts have consequently been made in the pharmaceutical and crop protection industries to find alternative ways of, obtaining early information about the ADME (absorption, distribution, metabolism, excretion) behavior of active agents. Since much of the ADME behavior is influenced by easily measurable physicochemical properties, or quantities that can be calculated from the chemical structure, the procedure has since been established for experimentally determining, or calculating, such quantities with a high throughput [H. van de Waterbeemd, D. A. Smith, K. Beaumont, D. K. Walker, J. Med. Chem. 44, 1-21 (2001)].

Examples of typical properties that are conventionally taken into account for this include lipophilicity, water solubility; permeabilities across synthetic membranes or cell layers, molecular weight and numbers of particular structural features, such as hydrogen donors and acceptors. The assessment of the substances then generally involves compliance with particular limits, which are conventionally obtained from empirical values or from the statistical distribution of the properties for commercially available products [C. A. Lipinski, F. Lombardo, B. W. Dominy, P. J. Feeney, Adv. Drug Delivery Rev. 23, 3-25 (1997) and C. M. Tice, Pest Management Sci. 57, 3-16 (2001)].

A disadvantage of this method is that rigid limits are considered for individual properties that are: only indirectly relevant. The ADME properties which are actually important, however, generally depend on a plurality of these quantities simultaneously, so that the tolerable limits of the individual quantities are also dependent on their value, and absolute limit values can therefore only be set very roughly.

U.S. Pat. No. 5,901,069 discloses a computer program product for at least partially automatic calculation of molecular quantities on the basis of a substance library. This method, however, does not make it possible to calculate ADME properties.

U.S. Pat. No. 5,680,590 discloses a simulation system for the calculation of physiological data in respect of pharmacokinetic and pharmacodynamic parameters. A disadvantage of this simulation system is that the calculation does not rely directly on the basis of molecular properties of a substance to be evaluated. This model is suitable only for training purposes and does not allow calculation of the ADME properties of a new substance.

It is an object of the invention to provide an improved method for calculating an ADME property of a substance, as well as a corresponding computer program and computer system.

BRIEF SUMMARY OF THE INVENTION

The object of the invention is respectively achieved by the features of the independent patent claims.

Preferred embodiments of the invention are specified in the dependent patent claims.

The invention can advantageously be used both for already synthesized substances and for "virtual structures" of substance libraries. For calculating the ADME properties, according to the invention, biophysical relationships between molecular and physicochemical properties of the substances and the ADME properties in question are used. The mathematical description is then carried out by using an analytical formula or, for more complex relationships, by using a numerical simulation.

A particular advantage of the invention is that the calculation of ADME properties is carried out directly on the basis of the molecular properties of the substance to be studied. A biophysical model is used for this purpose, into which the molecular properties are entered as input quantities. The biophysical model establishes a relationship between the molecular properties and the ADMIE property or properties. In this way, a direct conclusion is obtained about the ADME properties, rather than merely about correlating surrogate quantities as is the case in the prior art.

According to a preferred embodiment of the invention, the lipophilicity, the binding to proteins and the molecule size are used as molecular properties. For example, this makes it possible to model the absorption of active agents in a human, animal or plant organism. The lipophilicity is in this case described by distribution coefficients between a lipoid phase (for example octanol, edible-oil, hexane, phospholipid membranes) and water. For example, the molar mass or the molar volume may be used as a measure of the molecule size.

Since this is generally determined by a permeation process, and the permeability is known to depend on the lipophilicity and the size of the permeating molecule, inferences about the absorption rate can be drawn from these properties. Yet since the dependencies are opposite, higher molar masses may for example be tolerated with increasing lipophilicity in order to reach the same absorption rates. This fact, moreover, cannot be taken into account sufficiently in the prior art when using fixed limit values for optimum lipophilicity and molecule size.

The invention, however, allows the ADME properties to be deduced directly from the molecular properties, so that a calculation with improved accuracy is possible.

According to a preferred embodiment of the invention, the biophysical model is a physiologically based pharmacokinetic model. For studying the ADME properties of a substance, for example in the human body, the model comprises at least the organs essential to the study, for example the lung, liver and kidneys as well as the blood circulation. The various submodels of the organs are linked together by conservation of mass equations.

According to another preferred embodiment of the invention, the conservation of mass equations are expressed in the form of a system of differential equations, the input quantities of the system of differential equations being obtained directly from the calculated molecular properties.

According to another preferred embodiment of the invention, the input of the chemical structure of a substance to be studied is carried out into a database. To this end, for example, the chemical structure may also be represented in the form of a descriptor or a so-called fingerprint.

The input of the chemical structure may in this case be carried out decentrally from a client computer. The client computer is, for example, located directly at a chemist's workstation for the input of new chemical structures, for which the ADME properties are intended to be determined in advance.

The querying of this database is then carried out cyclically, for example by a server computer. As soon as the input of a new chemical structure has been identified by the server computer, the molecular properties of this chemical structure are determined automatically by a corresponding program start-up command.

As an alternative or in addition, the server computer may access a further database, in which the experimentally determined molecular properties of the substance are stored. After the molecular properties have been determined, they are entered into the biophysical model by, a further program start-up command, so that the calculation of the intended ADME properties is carried out automatically.

This process is preferably carried out repeatedly for various substances, for example with the same chemical parent substance. The results of the ADME calculations are then output in a structured form, for example sorted according to the value of a particular ADME property or sorted according to a weighted index of ADME properties.

According to another preferred embodiment of the invention, a statistical method is used for calculation of the molecular properties from the chemical structure, for example a QSAR or HQSAR method, or a method based on a neural network. Such methods for the determination of molecular properties—for example from a descriptor of the chemical structure—are known per se from the prior art.

For pharmacy uses, the invention makes it possible to calculate the following ADME properties in particular:
  absorbed fraction of a dose of the substance following oral application (absorbed fraction),
  concentration-time curves in the portal vein following oral application,
  free fraction in the plasma,
  organ/plasma distribution coefficient,
  blood/plasma distribution coefficient
  concentration-time curves in the blood plasma and in organs following oral or intravenous application,
  conventional pharmacokinetic parameters derived from the concentration-time curves, for example maximum concentration, time of max. concentration, distribution volume, half-lives.

For crop protection uses, the invention makes it possible to calculate the following ADME properties in particular:
  characteristic for rate of absorption into the leaf following spray application,
  characteristic for rate of absorption into an insect through the cuticle,
  characteristic for rate of distribution in the plant following leaf application (phloem mobility),
  characteristic for rate of distribution in the plant following root application (xylem mobility),
  concentration distribution between the organs of an insect.

The calculated data are either stored directly in a database or output in a table. The data provided in this way form the basis for ranking of the relevant substances or structures and selection of the candidates for further optimizations with the aid of this ranking.

For ranking, those properties which are crucial for the desired use of the active agents to be optimized should initially be selected. The evaluation is carried out manually with the appropriate data processing and visualization software. The ranking is in this case used to find the substances or structures which lie in the optimum range in the property distribution (for example the 10 substances with the highest absorption following oral application). If more than one property is taken into account in the ranking, then an index which contains it may be calculated (in the simplest case, the sum of the values of all the quantities), in which case weightings of the properties may also be carried out according to relevance.

As an alternative to manual evaluation, it is also possible to use output masks for the data; these carryout an automatic evaluation by utilizing the data to check, for each structure, whether particular values or combinations of values (indices) lie in an optimum range for the relevant use (display, for example using traffic-light colors). The project-specific rules are then stored under the analysis mask (for example in a table calculation program).

Preferred embodiments of the invention will be explained in more detail below with reference to the drawings, in which:

BRIEF DESCRIPTION OF THE FIGURES

FIG. 3 shows a table for the calculation of organ/blood distribution coefficients for the model in FIG. 2.

DETAILED DESCRIPTION OF THE INVENTION

Figure 1:
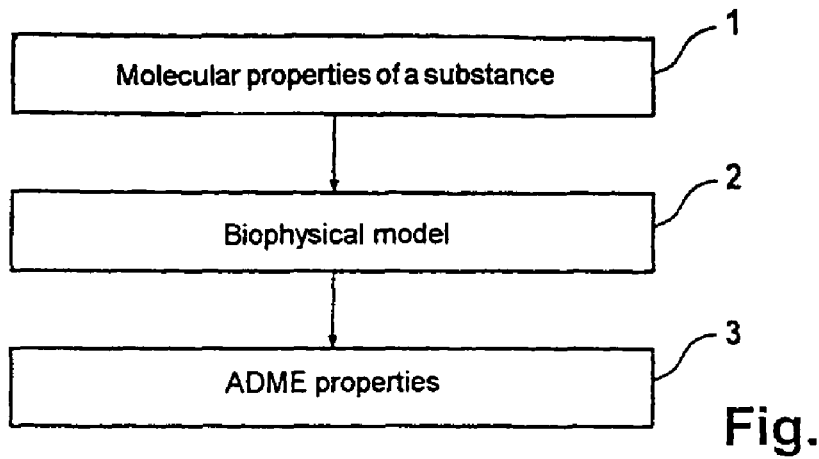
FIG. 1 shows a flow chart of the calculation of ADME properties from the molecular properties of a substance.

FIG. 1 shows a flow chart for the calculation of ADME properties of a substance. The molecular property of a substance is determined in step 1. This may be done experimentally if the substance has already been synthesized. Determination of the molecular properties may furthermore be carried out by a calculation.

To this end, methods which make it possible to calculate molecular properties from the chemical structure are known per se from the prior art. Examples of such methods are QSAR, HQSAR and neural networks. Descriptors or fingerprints of the chemical structure of the substance to be studied are used as an input quantity for such calculation methods.

In step 1, it is furthermore possible to access both experimentally determined molecular properties and molecular properties of the substance which have been determined by calculation. In this way, experimental methods can be supplemented with the calculation methods in order to determine the molecular properties.

The molecular properties of the substance which were determined in step 1 are entered into a biophysical model in step 2. The biophysical model establishes a relationship between the molecular quantities and the ADME properties of interest. It may, for example, be a physiologically based pharmacokinetic model. An embodiment of such a biophysical model will be explained in more detail below with reference to FIGS. 2 and 3.

The ADME properties are output from the biophysical model in step 3. A particular advantage in this case is that the ADME properties are determined directly from the molecular properties, and without the involvement of surrogate quantities that require interpretation. This allows a fully automatic procedure for calculation of the ADME properties.

Figure 2:
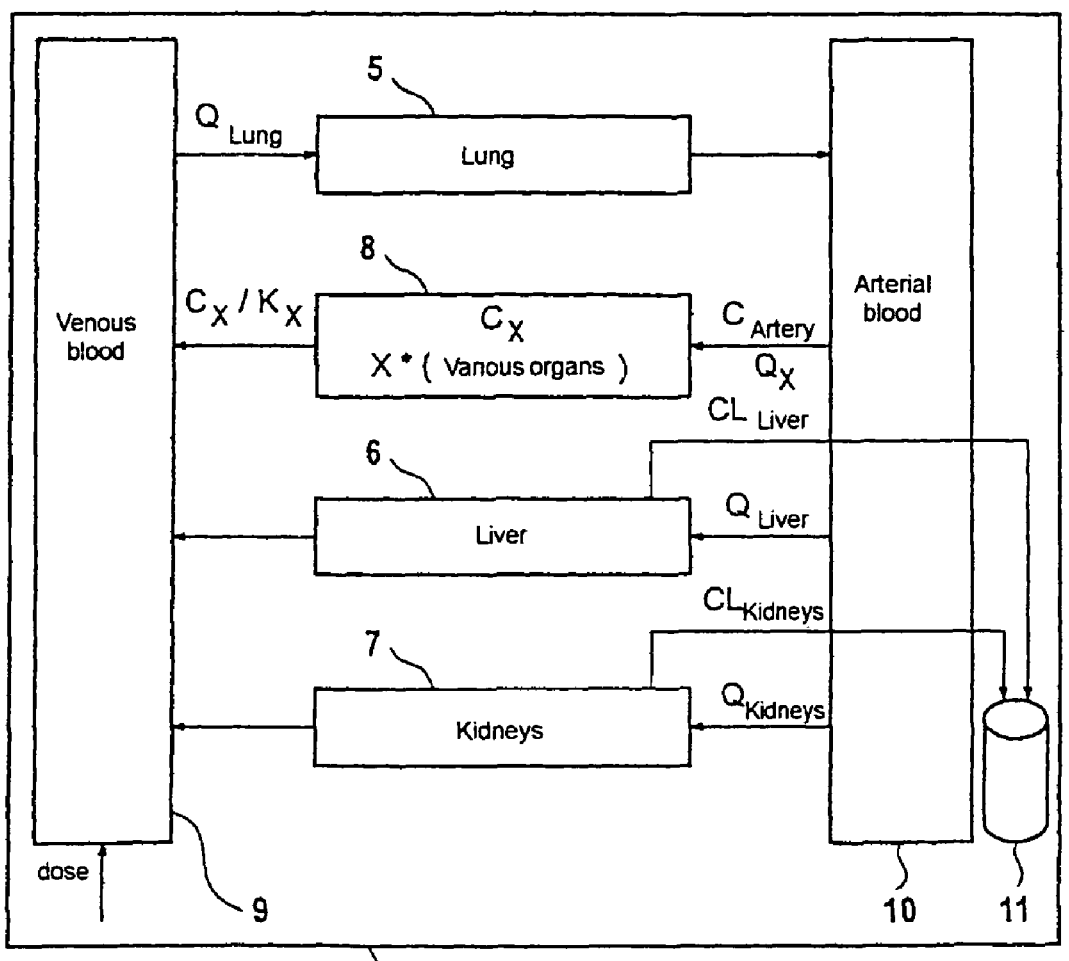
FIG. 2 shows an embodiment of a biophysical model for establishing a relationship between the molecular properties and the ADME properties.

FIG. 2 shows a biophysical model 4 of a warm-blooded animal, for example a human being. The biophysical model 4 contains a number of submodels for those organs that are most relevant to the distribution of the substance in the body. In the example of FIG. 2, these are the submodel 5 for the lung, submodel 6 for the liver, submodel 7 for the kidneys and submodels 8, respectively for various other organs X.

The submodels 5, 7, 8 are "interconnected" with one another by venous blood 9 and arterial blood 10. The venous blood 9 enters the submodel 5 for the lung, where it is converted into arterial blood 10. The arterial blood 10 then goes into the other submodels 6, 7 and 8, from which it reemerges as venous blood 9. The various submodels of the organs are thus "connected in parallel" by the venous blood 9 and the arterial blood 10.

The biophysical model 4 furthermore contains an excretion model 11 for the submodels 6 and 7, i.e. for the liver and the kidneys.

In the exemplary case of FIG. 2 which is being considered, the biophysical model is intended for modeling the time-dependent concentration distribution of a dose of the substance to be studied. The dose is in this case delivered via the venous blood 9, i.e. for example via the portal vein following oral application or by injection into a vein.

A corresponding table of empirical values may be accessed for the flow rate $Q_{lung}$ of venous blood 9, through the lung 5. Corresponding empirical values for the flow rates $Q_{liver}$, $Q_{kidneys}$ and $Q_x$ may likewise be accessed for the flow rates of arterial blood 10 through the other organ submodels 6, 7, 8.

The quantities $C_x$ are the concentration of the substance in the relevant organ X at a particular time. The parameter $K_x$ denotes the distribution coefficient of the substance between blood and the organ X in the equilibrium state. The parameters $CL_{liver}$ and $CL_{kidneys}$ denote the intrinsic excretion of the liver and the kidneys, respectively.

On the basis of the biophysical model 4, a mass equilibrium relation can be set up for each organ X by a differential equation of the following form:

$$V_x \cdot \frac{dC_x}{dt} = Q_x \cdot C_{ar} - Q_x \cdot \frac{C_x}{K_x}$$

$V_x$=volume of the organ X
$C_x$=concentration of the substance in the organ X
$Q_x$=flow rate of blood through the organ X
$f_u$=fraction of the substance which is not bound in plasma
$C_{ar}$=concentration of the substance which reaches the organ via the arterial blood
$K_x$=distribution coefficient of the substance between blood and organ X in the equilibrium state The parameter $f_u$ is calculated from the inverse of the distribution coefficient of the substance in equilibrium between blood plasma and water.

The corresponding differential equations for the liver and the kidneys contain an additional term, which describes the excretion of the substance. Such a differential equation is given below for the kidneys; similar considerations apply for the liver:

$$V_{ki} * \frac{dC_{ki}}{dt} = Q_{ki} * C_{ar} - Q_{ki} * \frac{C_{ki}}{K_{ki}} - \frac{CL_{ki}}{K_{ki}}$$

$V_{ki}$=volume of the kidneys
$C_{ki}$=concentration of the substance in the kidneys
$Q_{ki}$=flow rate of the blood through the kidneys
$f_u$=fraction of the substance which is not bound in plasma
$C_{ar}$=concentration of the substance which reaches the kidneys via the arterial blood
$K_{ki}$=distribution coefficient of the substance between blood and kidneys in the equilibrium state
$CL_{ki}$=intrinsic excretion of the kidneys An equation for the venous blood can be set up from this, and specifically by adding up all the "output" concentrations of the various organs and the intravenously delivered dose of the substance. The term $$\frac{CL_{ki}}{K_{ki}}$$

is dependent on the lipophilicity value of the substance, and can thus be determined from a molecular property.

The differential equation for the lung establishes a connection between the venous blood and the arterial blood. The corresponding equations are given below:

$$V_{ve} \cdot \frac{dC_{ve}}{dt} = \sum Q_x \cdot \frac{C_x}{K_x} - Q_{lu} \cdot C_{ve} + \text{dose} \cdot 1(t)$$

$$V_{lu} \cdot \frac{dC_{lu}}{dt} = Q_{lu} \cdot C_{ve} - Q_{lu} \cdot \frac{C_{lu}}{K_{lu}}$$

$V_{ve}$=volume of the venous blood
$C_{ve}$=concentration of the substance in venous blood delivered to the lung
$Q_x$=flow rate of blood through the organ X
$f_u$=fraction of the substance which is not bound in plasma
$C_x$=concentration of the substance in the organ X
$K_x$=distribution coefficient of the substance between blood and organ X in the equilibrium state
$Q_{lu}$=blood flow through the lung=$\Sigma$ of all blood flows
$V_{lu}$=lung volume
$C_{lu}$=concentration of the substance in the lungs
$K_{lu}$=distribution coefficient of the substance in equilibrium between blood and lungs
dose=dose of the substance which is delivered to the venous blood as a function of time t according to an input function I(t).

Knowledge of the various distribution coefficients in the equilibrium state is necessary in order to solve the resulting system of differential equations of the biophysical model 4. This can be determined from molecular properties of the substance which have been found experimentally or calculated beforehand.

In the course of the calculation, the distribution coefficients in equilibrium between fat and water ($K_{fat}$) and between protein and water ($K_{protein}$) can be determined for a substance. Said distribution coefficients are determined either computationally or experimentally; there are methods known per se from the prior art for both computational and experimental determination.

The organ compositions comprising the constituents water, fat and protein are furthermore utilized for the calculation. These can be found from the table according to FIG. 3. For various organs, the table of FIG. 3 indicates the total mass of the relevant organ as well as the absolute fractions in grams of water, fat and protein in the organ.

$F_{water}$, $F_{fat}$ and $F_{protein}$ can be determined from this, where
$F_{water}$=total mass of water in the organ/total mass of the organ
$F_{fat}$=total mass of fat in the organ/total mass of the organ
$F_{protein}$=total mass of protein in the organ/total mass of the organ The distribution coefficients of the substance between an organ and water in the equilibrium state ($K_{organ/water}$) can be calculated from this:

$$K_{organ/water} = F_{water} + K_{fat} \cdot F_{fat} + K_{protein} \cdot F_{protein} \quad (1)$$

The organ/blood or organ/plasma distribution coefficients can in turn be calculated from this:

$$K_{organ/blood} = K_{organ/water} / K_{blood/water} \quad (2)$$

$$K_{organ/plasma} = K_{organ/water} / K_{plasma/water} \quad (3)$$

The coefficients $K_{blood/water}$ and $K_{plasma/water}$ are likewise calculated according to Formula (1).

With the aid of the biophysical model 4 (cf. FIG. 2), the concentration of the substance in a particular organ X ($C_x$) as well as the concentration of the substance in the arterial blood ($C_{ar}$), and also the time profile of this concentration, can thus be determined directly from the molecular properties $K_{fat}$ and $K_{protein}$ of the substance by solving the aforementioned system of equations.

Figure 4:
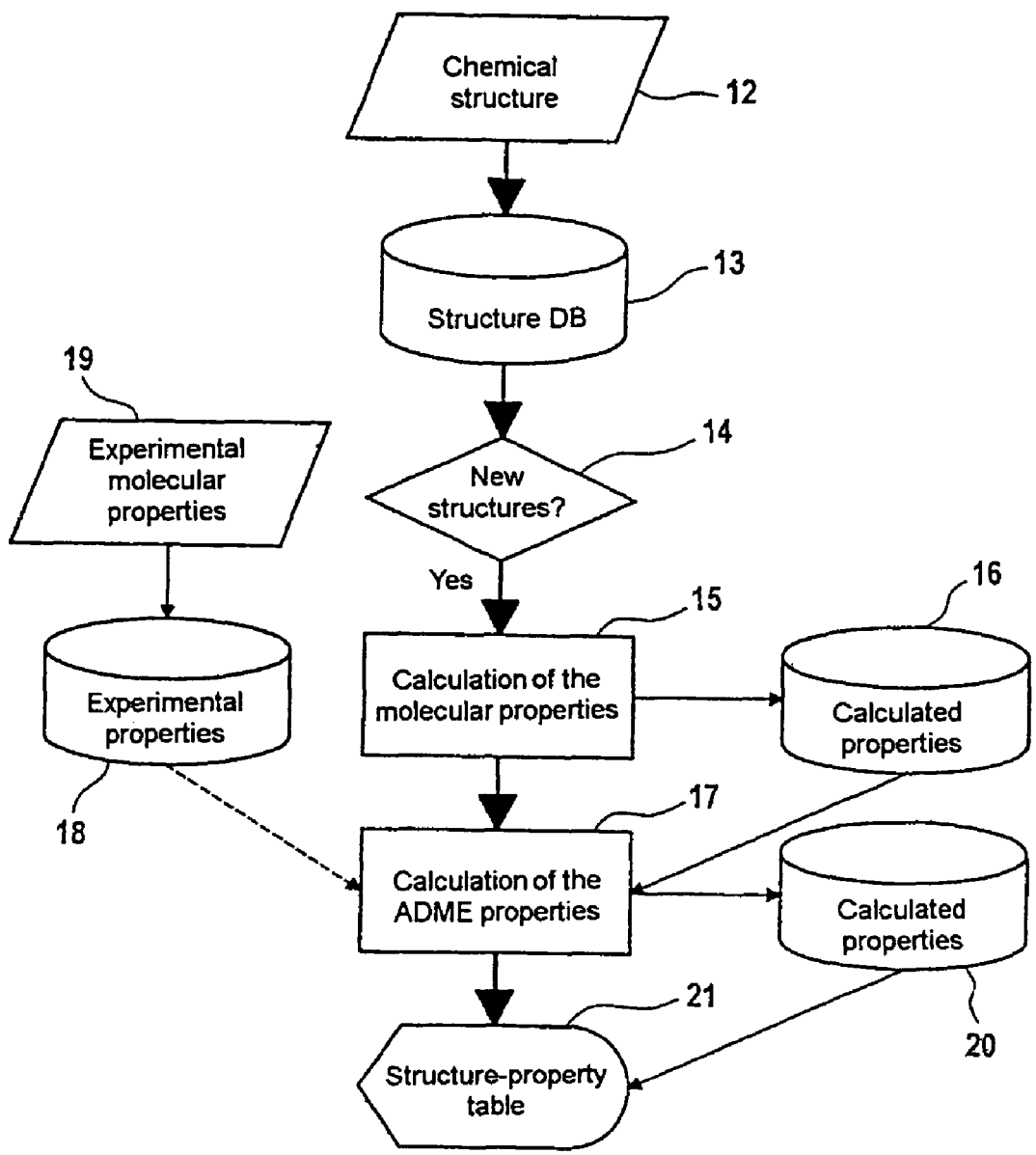
FIG. 4 shows an embodiment of a computer system according to the invention.

FIG. 4 shows a block diagram of a computer system for the calculation of ADME properties of a substance.

A file 12 contains the chemical structure of the substance, for example in the form of a so-called descriptor or a fingerprint. The file 12 is entered manually by a chemist, or is a part of a substance library of chemical structures whose ADME properties are to be determined.

The file 12 is entered into a database 13. The database 13 is used to store files 12 describing chemical structures. The file 13 is cyclically queried by a program 14, and specifically as to whether a new file 12 has been entered in the period of time since the previous query.

For example, the input of the file 12 may be carried out by a client computer. The database 13 is located on a server computer, for example, likewise the program 14 which cyclically queries the database 13. A distributed system can be produced in this way.

If the program 14 identifies that a new file 12 has recently been entered into the database 13, then the program 14 automatically starts a program 15 for calculation of the molecular properties of the substance described by the file 12. The molecular properties calculated by the program 15 are temporarily stored in a file, or are stored in a database 16.

After the molecular properties have been calculated and they have been stored in the database 16, the program 15 automatically starts a program 17 for the calculation of one or more ADME properties of the substance. To this end, the program 17 accesses the database 16 in order to call up the molecular properties of the substance which were calculated earlier by the program 15.

As an alternative or in addition, the program 17 accesses a database 18 which contains further, experimentally determined molecular properties of the substance. This presupposes that the substance has already been synthesized, so that experimentally determined molecular properties of the substance in a file 19 can be entered into the database 18.

The ADME properties calculated by the program 17, on the basis of the molecular properties stored in the database 16 and/or the database 18, are stored in a database 20. A program 21 accesses the database 20 in order to generate a structured output. This may be done in the form of a tabular output in spreadsheet form. The output may also take place sorted according to particular ADME properties.

The invention claimed is:

1. A computer program stored on a computer readable medium for carrying out the method of calculating one or more ADME (Absorption, Distribution, Metabolism, Excretion) properties of a compound, the method comprising the following steps:
    (a) inputting one or more molecular properties of the compound into a biophysical model representing a physiologically based pharmacokinetic model, the biophysical model describing a relationship between the one or more molecular properties and the one or more ADME properties,
    (b) determining the one or more ADME properties based on the one or more molecular properties in the biophysical model, and
    (c) outputting the one or more ADME properties to a user, wherein the biophysical model comprises a physiologically based pharmacokinetic submodel for each of a plurality of organs, the submodels being connected to one another by a blood flow model and the relationship between the organs and blood being described by mass equilibrium equations.

2. A computer system including a computer and the computer program of claim 1 for carrying out the method of calculating one or more ADME (Absorption, Distribution, Metabolism, Excretion) properties of a compound.

3. The computer system of claim 2 further comprising,
    (a) a first database for input of the chemical structure of a compound,
    (b) a computer that performs the following functions:
        (i) cyclic querying of the database with respect to an input of a chemical structure,
        (ii) automatically calculating one or more molecular properties of the compound, based on its chemical structure, after the input of the chemical structure has been detected by the cyclic querying, and
        (iii) automatically calculating one or more of the ADME properties.

4. The computer system of claim 3, further comprising a second database storing additional, experimentally determined molecular properties of the compound, wherein the automatic calculation of the ADME property is carried out on the basis of the calculated molecular properties or the additional, experimentally determined molecular properties or both.

5. The computer system of claim 3, wherein the computer further performs the function of outputting the calculated ADME properties of various compounds in a structured form.

6. The computer system of claim 5, wherein the structured form is a table.

7. The computer system of claim 5, wherein the structured form is a relational table.

8. The computer system of claim 3, wherein the computer further performs the function of calculating an index from the ADME properties, in order to sort various compounds.

\* \* \* \* \*